United States Patent
Martin et al.

(10) Patent No.: US 6,372,542 B1
(45) Date of Patent: Apr. 16, 2002

(54) METHOD OF COMPONENT MANUFACTURE

(75) Inventors: Hans Göran Evald Martin, Delsbo; Per Ove Öhman, Uppsala, both of (SE)

(73) Assignee: Åmic AB, Uppsala (SE)

(*) Notice: Subject to any disclaimer, the term of this patent is extended or adjusted under 35 U.S.C. 154(b) by 0 days.

(21) Appl. No.: 09/622,398
(22) PCT Filed: Feb. 4, 1999
(86) PCT No.: PCT/SE99/00146
 § 371 Date: Oct. 19, 2000
 § 102(e) Date: Oct. 19, 2000
(87) PCT Pub. No.: WO99/41772
 PCT Pub. Date: Aug. 19, 1999

(30) Foreign Application Priority Data

Feb. 17, 1998 (SE) ................................. 9800462

(51) Int. Cl.$^7$ .......................... H01L 21/66; H01L 21/44
(52) U.S. Cl. .................... 438/106; 438/14; 438/107; 438/117
(58) Field of Search .................... 438/14, 106, 107, 438/108, 110, 117; 359/81, 82; 361/760; 257/690, 692, 698

(56) References Cited

U.S. PATENT DOCUMENTS

| | | | | |
|---|---|---|---|---|
| 6,117,710 A | * | 9/2000 | Mostafazadeh et al. | 438/123 |
| 6,121,118 A | * | 9/2000 | Jin et al. | 438/460 |
| 6,159,776 A | * | 12/2000 | Terasawa | 438/137 |
| 6,171,887 B1 | * | 1/2001 | Yamji | 438/106 |
| 6,251,703 B1 | * | 6/2001 | Van Campenhout et al. | 438/106 |
| 6,265,245 B1 | * | 7/2001 | Farnworht et al. | 438/107 |
| 6,271,048 B1 | * | 8/2001 | Reilich et al. | 43/14 |
| 6,274,931 B1 | * | 8/2001 | Jeon et al. | 257/734 |

* cited by examiner

Primary Examiner—Michael Lebentritt
(74) Attorney, Agent, or Firm—Ostrolenk, Faber, Gerb & Soffen, LLP (57) ABSTRACT

The present invention relates to a method of producing an electric, electronic, electromechanical and/or mechanical component (12), where the component substrate is given a three-dimensional structure (3") or configuration, and where said substrate is adapted for further treatment or processing to form the component (12). The substrate is formed by shaping said substrate against a die or mold, such as by molding, pressing, extruding or embossing said substrate, wherewith the precision necessary with respect to said component in the three-dimensional structure is achieved by means of a micromechanical working process when producing the die or mold.

31 Claims, 4 Drawing Sheets

METHOD OF COMPONENT MANUFACTURE

FIELD OF INVENTION

The present invention relates to a method of producing an electric, electronic, optic and/or mechanical component in which the component substrate is given a three dimensional structure or shape and the substrate then further worked to build the component.

DESCRIPTION OF THE BACKGROUND ART

It has long been known to construct different types of components, such as sensors and mechanical units, with the aid of methods with which the base of the component is formed from silicon, quartz or some other more or less expensive material. In some instances, the material can be worked micromechanically so as to give the material certain three-dimensional forms or structures. These substrates are then processed by adding material to or removing material from certain areas, for instance areas that have been defined with the aid of lithographic techniques.

For reasons of a process/technical nature, traditional bases are almost always comprised of a circular disc of substrate material. Subsequent to working the disc micromechanically so as to form the three-dimensional structure, the disc can be subjected to such processes as lithographic processes, PVD processes (physical Vaporised Deposition), CVD processes (Chemical Vaporised Deposition), doping, ion-implantation, or various types of etching processes (ion, chemical, plasma etching processes, etc.) A desired result can also be achieved by combining two or more of these processes.

A disc of this nature is dimensioned to enable a plurality of components to be built up simultaneously on one and the same disc, which is then divided into respective components.

Some of the process steps require unprecedented precision while other process steps are less critical. The cost of passing a quartz or silicon disc through all process steps is very high, although because precision is very high the individual units can often be made small and therewith enable many units to be manufactured at one and the same time and therewith keep the price of each unit relatively low.

However, these conditions do not always apply, such as when certain physical measurements must be observed for instance. Examples in this respect are when a unit includes a connection for an optical fibre of specific measurements, sample volumes for chemical or biochemical analyses, optical path lengths for gas sensors, and so on.

In these cases, the combination of space-demanding or area-demanding functions and precision and process requirements can cause the cost of the final component to be relatively high in comparison with what the component achieves.

Many examples of components that are produced by subsequent treatment of a three-dimensional structure to form the component are known to the art.

The publication "Combustible Gas Sensor Fabricated With 3D-Micro Technology" by Tsing Cheng, Landis & Gyr Corporation, Central Research and Development Lab., CH 6301 Zug, Switzerland, illustrates an example of how a sensor, a compact three-dimensional thermopile can be built by microtechnology.

The substrate used in this document is a silicon disc (FIG. 5a). A grating or a number of ridges is/are provided on the surface of the disc. The grating is provided with two mutually different conductors at mutually different oblique angles (FIG. 5c), thereby forming a number of mutually sequential junctions from one conductor to the other. This procedure results in a thermopile.

The publication also discloses the possibility of using a polyimide as material for building the three-dimensional structure (FIG. 5b).

It should also be mentioned that the publication "Microstructures and Replication Techniques" by Olle Larsson, Industrial Microelectronics Center (IMC), Stockholm, Sweden published in conjunction with a national conference "Micro Structure Workshop 1996" held in Uppsala, Sweden, Mar. 26–27, 1996, describes how micromechanically produced models can be replicated by creating a mould from the model and then producing a plurality of copies or replicas of the model with the aid of the mould. The document describes a number of different ways in which this can be achieved.

It should also be mentioned that Swedish Patent Applications 93 02051 9 and 95 00849 6 teach methods of replicating channels that are intended to hold samples for a biochemical analyser that is based on electrophoretic separation. These channels are comprised of passive components and the electric field required for an analysis is applied with the aid of external electrodes.

SUMMARY OF THE INVENTION

TECHNICAL PROBLEMS

When taking into consideration the technical deliberations that a person skilled in this particular art must make in order to provide a solution to one or more technical problems that he/she encounters, it will be seen that on the one hand it is necessary initially to realise the measures and/or the sequence of measures that must be undertaken to this end, and on the other hand to realise which means is/are required in solving one or more said problems. On this basis, it will be evident that the technical problems listed below are highly relevant to the development of the present invention.

When considering the present state of the art, as described above, and when taking a starting point from a method of manufacturing an electric, electronic, electromechanical and/or mechanical component where the component substrate is given a three-dimensional structure or shape and the substrate then subjected to further treatment to form the component, it will be seen that a problem resides in realising how the costs of producing this three-dimensional structure for components that have high accuracy requirements regarding the dimensioning of the three-dimensional structure and where respective components are of such a large size that only one or a few components can be produced on each disc of traditional size, can be kept at a level which is reasonable in relation to what the component or components is/are able to achieve.

Another technical problem is one of realising how such manufacture can be achieved without needing to micromechanically work each individual component.

Another technical problem is one of realising how certain limitations that exist in traditional substrates, such as silicon and quartz substrates, can be overcome and how components that require substrate properties that do not exist in, for instance, silicon or quartz substrates can be manufactured with the precision required and at reasonable costs.

Still another technical problem resides in overcoming the prejudices that exist in traditional component manufacture with regard to the use of materials other than silicon and quartz in lithographic processes, metallising processes, doping processes, etching processes, etc.

Yet another technical problem is one of realising that in addition to said component other components and/or necessary conductor paths can be produced from a three-dimensional structure by subsequent processing of said structure.

Another technical problem is realising that a three-dimensional structure can be worked to provide mechanical parts, such as snap-fastener means, outwardly jutting parts or recesses by means of which said component can be fitted to a base structure, in addition to producing said component.

It will also be seen that a technical problem is one of realising how a micromechanically worked structure can be divided into a number of three-dimensional structures that are intended for subsequent working and that have precise dimensions.

Another technical problem is one of realising the manufacturing advantages and economic advantages that are afforded by transferring an exact, micromechanically manufactured three-dimensional structure in silicon or quartz to a plurality of three-dimensional structures in a polymeric material.

Another technical problem is one of adapting a method according to the present invention to the production of different specific components, such as thermocouples, pressure sensors, electro-optical coupling units for optical sensors or units combined with electric signal processing or the establishment of electric contacts.

SOLUTION

With the intention of solving one or more of the aforesaid technical problems, the present invention takes as its starting point a method of producing an electric, electronic, optical and/or mechanical component where the component substrate is given a three-dimensional structure or shape and the substrate then processed or worked to form said component. In brief, instead of using a flat silicon plate, which may be disc-shaped, as a substrate structure, certain geometrical details necessary for the component are formed on a silicon or quartz plate by means of a micromechanical method, in accordance with the invention. These geometric details are then replicated on a polymeric plate, which may also be disc-shaped. This enables those costly process steps that need to be carried out at great precision to be restricted to steps in which such precision is most necessary. This short cut enables the costs of certain components to be kept at a low level and in other cases further complexities that would otherwise had been impossible to achieve can be added.

The three-dimensional structure formed by the geometrical details can be transferred from the silicon plate or quartz plate to the polymeric plate by shaping, such as moulding, pressing, extruding or embossing, against a die or mould.

With the intention of making the manufacture of a component more effective, it is proposed in accordance with the invention that the component is produced on a limited surface area or region and that electric conductor paths and/or further electric and/or electronic components are produced on this delimited surface area in the same way, thereby enabling surrounding parts necessary for the component to be integrated therewith.

It is also possible in accordance with the invention to produce mechanical parts, such as snap-fastener means, outwardly jutting parts and recesses, by means of which the components can be fitted to a substrate.

The present invention proposes two basic methods of enabling a three-dimensional structure to be replicated.

According to a first method, at least that part of the die or mould which corresponds to the component is produced by shaping said die to a model of the structure, e.g. by moulding or electroplating. The model is produced by micromechanically working a material that is suitable in this respect, wherein the three-dimensional structure and/or the configuration of the model is chosen to correspond to the desired component-associated surface parts, electric conductor paths and/or other electric and/or electronic circuits.

According to a second method, at least that part of the die or mould which corresponds to the component is produced by micromechanically working directly a material that is suitable in this respect, and the three-dimensional structure of the die or mould is made complementary to desired component-associated surface parts, electric conductor paths and/or other electric and/or electronic circuits.

The original shape or structure on which the final three-dimensional structure is based may alternatively be obtained by, e.g., electron-beam lithography, thereby enabling the creation of necessary structure for building, e.g., diffractive optical elements.

As earlier mentioned, it is proposed in accordance with the invention that the component substrate is comprised of a polymeric material, but that the material suitable for said micromechanical working process is comprised of silicon or quartz. This enables the three-dimensional structure to be produced with the necessary precision by micromechanically working a material suitable to this end, and then replicating this structure with retained precision on a substrate that is economically advantageous, particularly in those instances when it is necessary for the component concerned to include physical measurements that result in a relatively large component.

According to the present invention, a thus produced three-dimensional structure can be further worked with the aid of different processes, such as lithographic processes, PVD processes, CVD processes, doping, ion-implantation processes, or etching processes, such as ion, chemical, or plasma etching processes.

According to one embodiment of the invention, these is applied a process at specific angles relative to the three-dimensional structure so as to obtain shadowing effects through which processed and non-processed surface regions are formed.

It is proposed in this respect that two or more application angles be used to form a pattern of mutually different processed regions.

Said further treatment or working processes may be comprised of a combination of one or more of the earlier described processes.

Examples of components that can be obtained through an adaptation of a method according to the present invention are, for instance, thermocouples, pressure sensors, electro-optical coupling units or a channel structure for a biochemical analyser. Examples of such components will be made more apparent in the following description of proposed embodiments.

ADVANTAGES

Those advantages that are primarily afforded by a method according to the present invention reside in the ability to produce in a cost effective manner components whose manufacture require a three-dimensional structure that can only be obtained by a micromechanical working process and where the components include physical measurements that only permit one or a few components to be produced with each substrate plate when practising traditional techniques.

This method opens the possibility of producing components that have hitherto been considered too costly in relation to what the components can achieve. The method therewith also opens a completely new field for the manufacture of components that enables components to be produced that have hitherto never been produced. The method can thus provide a decisive breakthrough in the manufacture of many different types of component.

The present invention also provides the advantage of enabling the peripheral elements required by the component to be readily integrated therewith, such as additional components, electric conductor paths or mechanical elements such as snap-fastener means, outwardly projecting surfaces or recesses intended for mounting the component on a substrate surface.

The primary characteristic features of an inventive method are set forth in the characterising clause of the following Claim 1.

BRIEF DESCRIPTION OF THE DRAWINGS

A method comprising features characteristic of the present invention will now be described in more detail by way of example and with reference to the accompanying drawings, in which.

DETAILED DESCRIPTION OF EMBODIMENTS AT PRESENT PREFERRED

Figures 1, 2, 3:
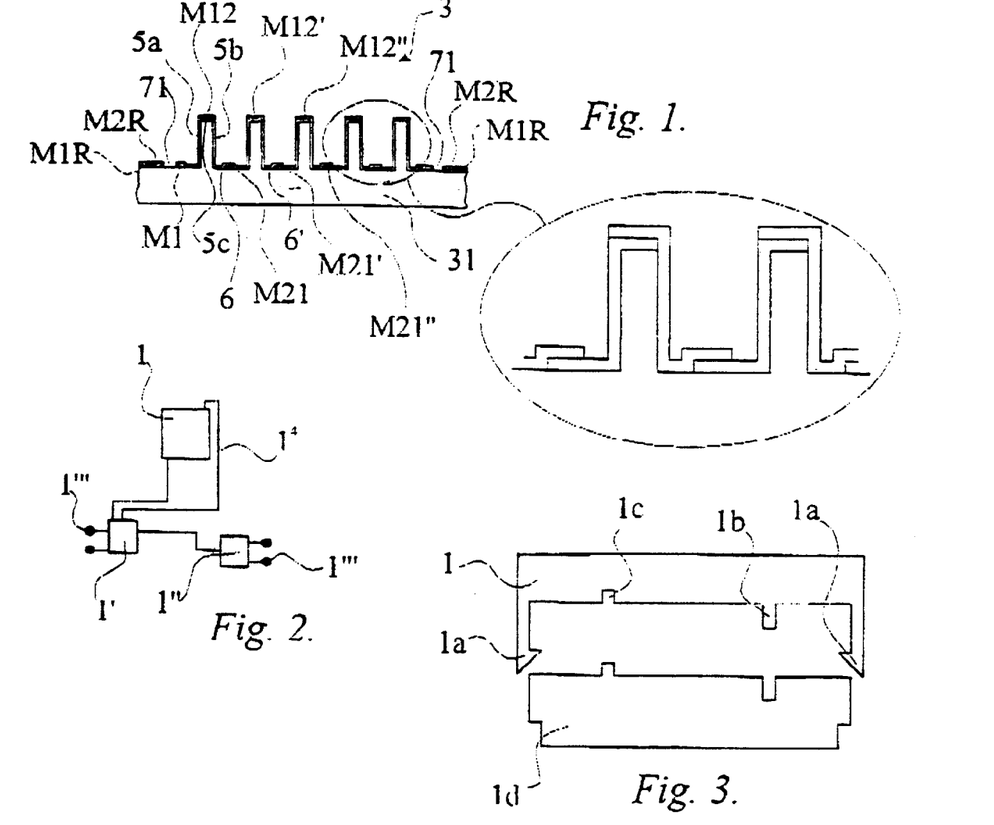
FIG. 1 illustrates a component in the form of a detector that includes two layers of mutually different metals that form a number of series-connected thermocouples.
FIG. 2 is a schematic, highly simplified illustration of a possible conductor path, electric and/or electronic circuits and connection pads that can be formed together with a component in accordance with the present invention.
FIG. 3 is a schematic and highly simplified illustration of mechanical parts that can be formed together with a component in accordance with the present invention.

FIG. 1 thus shows a method of producing an electric, electronic optical and/or mechanical component.

The description is directed to a thermocouple 1 as an example of a component produced in accordance with the method. Reference is made to Swedish Patent Application 98 00462-5 for a more detailed description of such a thermocouple.

As shown in FIG. 1, a substrate 2 for the thermocouple 1 has a three dimensional structure or configuration 3 and is adapted for further treatment or processing so as to form the end produce, i.e. the thermocouple.

As shown in FIG. 1, the three-dimensional structure 3 for the thermocouple is produced on a delimited surface region, and that electric conductor paths and/or further electric and/or electronic components can be produced on this delimited surface region in mutually the same way.

These further components may comprise an amplifier $1'$, a voltage unit $1''$, correction pads, connection terminals $1'''$, or an electric conductor path $1^4$, etc., as shown in FIG. 2.

The thermocouple 1, or the component, may also be provided with mechanical parts, such as snap-fastener means 1a, projections 1b or recesses 1c which enable the component to be fitted to a base structure 1d, in accordance with FIG. 3.

It will be understood that FIG. 3 is intended solely to illustrate how the component can be provided with various mechanical parts in accordance with the invention. For instance, the snap-fastener means 1a shown in FIG. 3 are difficult to form in a moulding operation. It will be obvious to the skilled person that a component can be provided with different mechanical parts with the aid of one or more of the various processes described in the descriptive part of this document.

According to the present invention, the substrate 2 is produced by shaping the substrate, such moulding, pressing, extruding or embossing said substrate against a die or mould $2'$ (FIG. 4a), where at least a part of the die or mould that corresponds to the component 1 is produced by shaping, such as moulding or electroplating (according to FIG. 4b), against a model $2''$ of the structure, and where the model $2''$ is produced by micromechanically working a material that is suitable in this respect.

The three-dimensional structure and/or configuration of the model $2''$ is chosen to correspond to desired component-associated surface parts, electric conductor paths and/or further electric and/or electronic circuits.

Figure 4A:
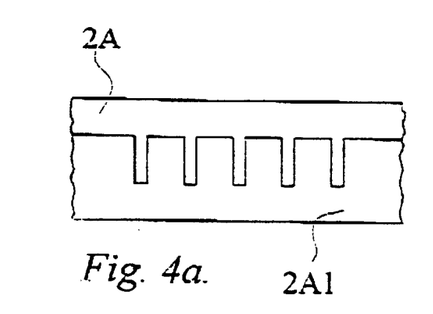
FIGS. 4a and 4b illustrate schematically and in side view how a detector-adapted base structure can be formed from a mould and a model.
Figure 4B:
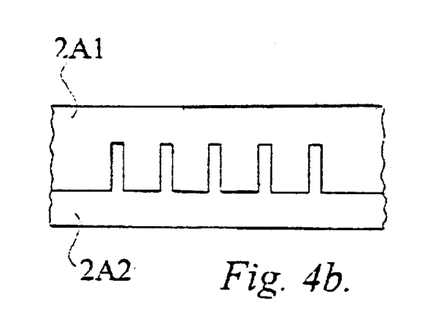

As will be seen from FIG. 4a, the substrate 2 may alternatively be produced by shaping such as moulding, pressing, extruding or embossing, against a die or mould $2'$ where at least a part of the die that corresponds to the component 2 is produced by micromechanically working a material that is suitable in this respect, and where the three-dimensional structure of the die or mould $2'$ is complementary in relation to desired component-associated surface parts, electric conductor paths and/or further electric and/or electronic circuits. In order to enable the substrate to be formed or shaped in accordance with the above, it is proposed in accordance with the invention that the substrate 2 consists of a polymeric material. The advantages of a polymeric substrate is that the substrate will be electrically insulating and have a high thermal resistance, which is basically very beneficial with regard to the manufacture of certain components.

Silicon and quartz are materials that can be conveniently worked micromechanically.

Different processes can be used to subsequently work or process the three-dimensional structure 3, these processes depending on the nature of the component to be produced. According to the invention, this subsequent working or treatment of the three-dimensional structure may include lithographic processes, PVD processes, CVD processes, various types of doping processes, ion-implantation or an etching process, such as an ion etching process, a chemical etching process or a plasma etching process.

Subsequent processing of the three-dimensional structure 3 may also include further mechanical working processes. For instance, because the substrate plate is held firmly in a vacuum chuck during certain of the processes to which it is subjected it may be convenient from a process/technical aspect to drill any holes that are required after these processes. Sawing or dividing a substrate plate into individual components is also a subsequent mechanical working operation.

It will also be understood that the three-dimensional structure can be worked also in other stages of the process. For instance, in addition to micromechanically working the die or the model, it may also be appropriate to work the die or model by some other method, such as to work said die or model lithographically or mechanically in order to give to the die or model further dimensions associated with the three-dimensional structure.

In the case of the illustrated embodiment, where the component is comprised of a thermocouple, a PVD process is used to coat the three-dimensional structure with one or more metal layers.

Figure 5:
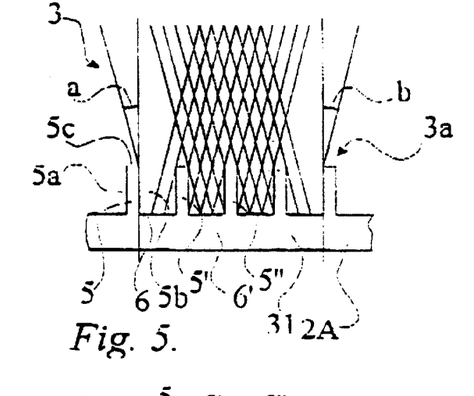
FIG. 5 is a schematic, somewhat enlarged side view of a detector according to the present invention.

According to FIG. 5, the metal layers are applied at a specific application angle in relation to the three-dimensional structure, whereby metal-coated surface regions and non-coated surface regions are formed by virtue of the shadowing effects that are achieved.

This concept of employing a specific application angle in relation to the three dimensional structure can also be used in processes other than the PVD process, in order to create processed and non-processed surface regions through the shadowing effects obtained.

It will be shown in the following that two or more application angles can be used, so as to create a pattern of different processed regions.

It is also possible for said further treatment to consist in a combination of one or more treatment processes in accordance with one of the earlier described processes.

The manner in which thermocouple can be constructed in accordance with the inventive method is described below, with the intention of enabling the present invention to be understood more readily.

In the case of this embodiment, a first and a second layer of electrically conductive metal are applied to the surface region or surface regions of the three-dimensional structure.

As illustrated in FIGS. 1 and 5, the layer of first metal M1 is applied to the three dimensional structure 3 for the non-electrically conductive substrate 2 at a first application angle "a" which is other than 90°, while the layer of said second metal M2 is applied to the three-dimensional structure 3 at a second application angle "b" which is also other than 90° but different to said first application angle "a".

The first and the second metal layers M1, M2 are thus caused to overlap one another within discrete detector-associated surface parts M12, M12', M12", M21, M21', M21", whereby the three-dimensional structure 3 and/or the die or mould provided with such an electrically conductive coating will function as one or more thermocouples.

To this end, the three-dimensional structure includes a plurality of so-called conductive ridges 5, 5', 5". Each of the conductive ridges has a first side surface 5a, a second side surface 5b and an upper surface 5c, and an intermediate so-called conductive surface 6 between respective mutually adjacent ridges 5, 5'.

The expression "conductive ridges" may be slightly misleading when the topographical structure has the form of a greatly diminished "tower block area", i.e. when the structure is comprised of a plurality of narrow rods and the rods in one row (or column) are slightly off-set in relation to the rods in an adjacent row with the various rods having mutually different heights.

The first angle "a" shall be adapted so that the first side surface 5a and at least a part of the upper surface 5c of respective conductive ridges 5, 5', 5", and at least a part of the intermediate conductive surfaces 6 will be coated with the layer of said first metal M1, while the second angle "b" shall be adapted so that the second side surface 5b and at least part of the upper surface 5c of respective conductive ridges 5, 5', 5", and at least a part of the intermediate conductive surfaces 6 will be coated with the layer of said second metal M2, in accordance with FIG. 1.

The first and the second angles "a", "b" shall also be adapted so that the metal layers overlap and form the electric contact M12, M21 with the first metal layer M1 on the upper surface 5c of respective conductive ridges 5, 5' and on the intermediate conductive surfaces 6, 6', such that the metal layers M1, M2 will form the series of electrically interconnected junctions M12, M12', M12", M21, M21', M21" between the first and the second metals M1, M2.

FIG. 1 shows a series of thermocouples formed in this way, said thermocouples comprising a plurality of ridges. In order to obtain an electrically functioning detector 1, it is necessary to electrically isolate all thermocouples from surrounding metal layers, i.e. to isolate the metal layers M1, M2 within the detector-associated surface electrically (at 71) from the metal layers M1R, M2R on the surrounding surface.

Figure 6:
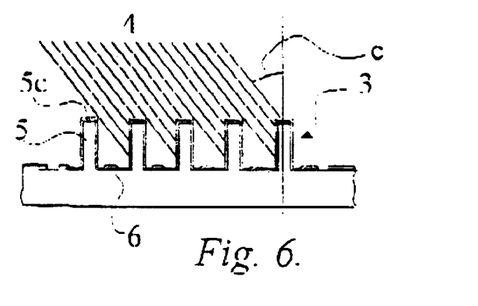
FIG. 6 is a simplified side view illustrating how a detector can be aligned or positioned in relation to a chosen angle of incidence of incident light rays.

According to the present invention, the component or the detector 1 is aligned relative to the angle of incidence "c" of the incident electromagnetic radiation or the light rays 4 to be detected by the detector, by positioning the detector 1 relative to incident light rays 4 so that said rays will irradiate the upper surface 5c of respective conductive ridges and so that the intermediate conductive surfaces 6 will be shadowed from incident light rays 4 by the conductive ridges, as shown in FIG. 6.

Figure 7:
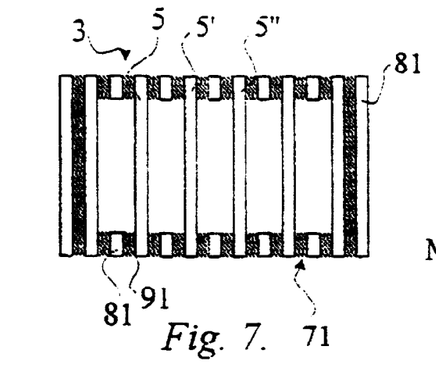
FIG. 7 illustrates schematically and from above how a detector can be isolated electrically from a surrounding metal layer.
Figure 8:
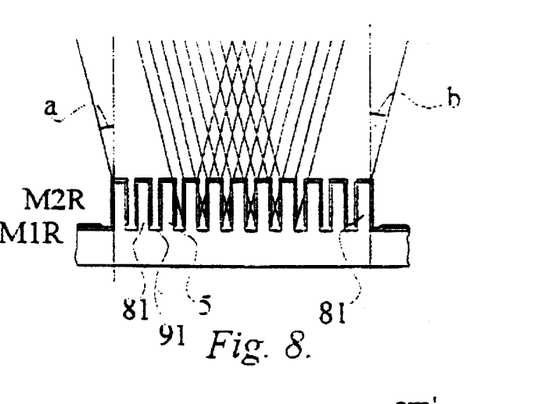
FIG. 8 illustrates schematically and in side view how a detector can be isolated electrically from a surrounding metal layer.

As shown in FIGS. 7 and 8, the electrical insulation 71 between the detector 3 and surrounding metal layers M1R, M2R is achieved by virtue of so-called insulating ridges 81 having mutually adjacent so-called insulating surface 91 and belonging to the three-dimensional structure are positioned in relation to one another and also in relation to the conductive ridges 5, 5', 5" and in relation to the first and the second angles "a", "b" such that the insulated surfaces 71 will not be coated with said first and second metals.

FIGS. 7 and 8 also illustrate the formation of a column of ridges. It is desirable to provide a large number of series-connected junctions from one metal layer to the other, in order to enhance the resolution or sensitivity of the detector 1. If the number of series-connected junctions is increased, the detector surface will obtain a pronounced oblong shape. For reasons of measuring technology, however, it is desirable for the detector surface to have an essentially square shape.

Figure 9:
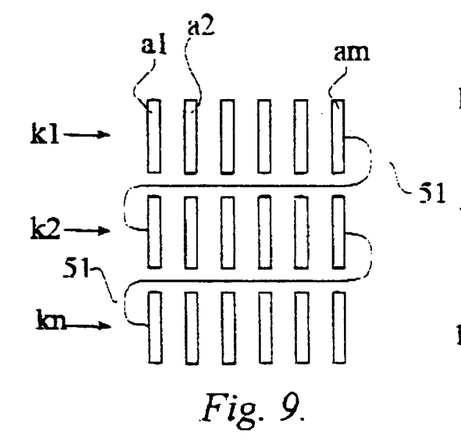
FIG. 9 illustrates schematically and from above a detector that includes several electrically interconnected columns of electrically conductive ridges.

Accordingly, it is proposed in accordance with the invention that the conductive ridges are given a configuration in which they form n-number of columns of mutually parallel conductive ridges, here referenced column 1 (k1), column 2 (K2), etc., up to column "n" (kn), where each column includes m-number of conductive ridges, here referenced ridge 1 (a1), ridge 2 (a2), etc., up to ridge "m" (am), and where "m" may be different for respective columns.

In order for the ridges of respective columns to form a coherent series of interconnections, it is proposed in accordance with the invention that the "m"th ridge "am" in each column, with the exception of the last column "kn", is connected electrically (at 51) with the first ridge "a1" of the next column in line.

Junctions are therewith formed between the first and the second metals belonging to all conductive ridges within all columns in a common series of electrically interconnected junctions.

Figure 10:
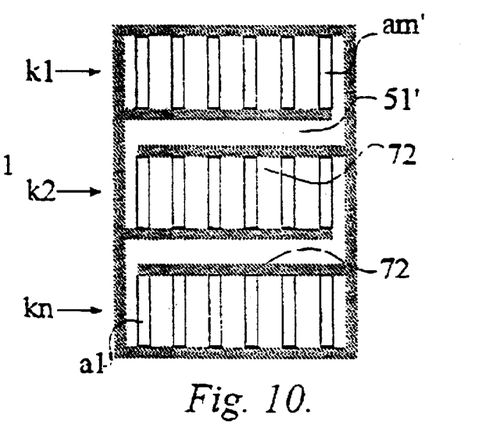
FIG. 10 illustrates schematically and from above a detector according to FIG. 9 where the columns are interconnected electrically by means of electrically conductive surface sections.
Figure 11:
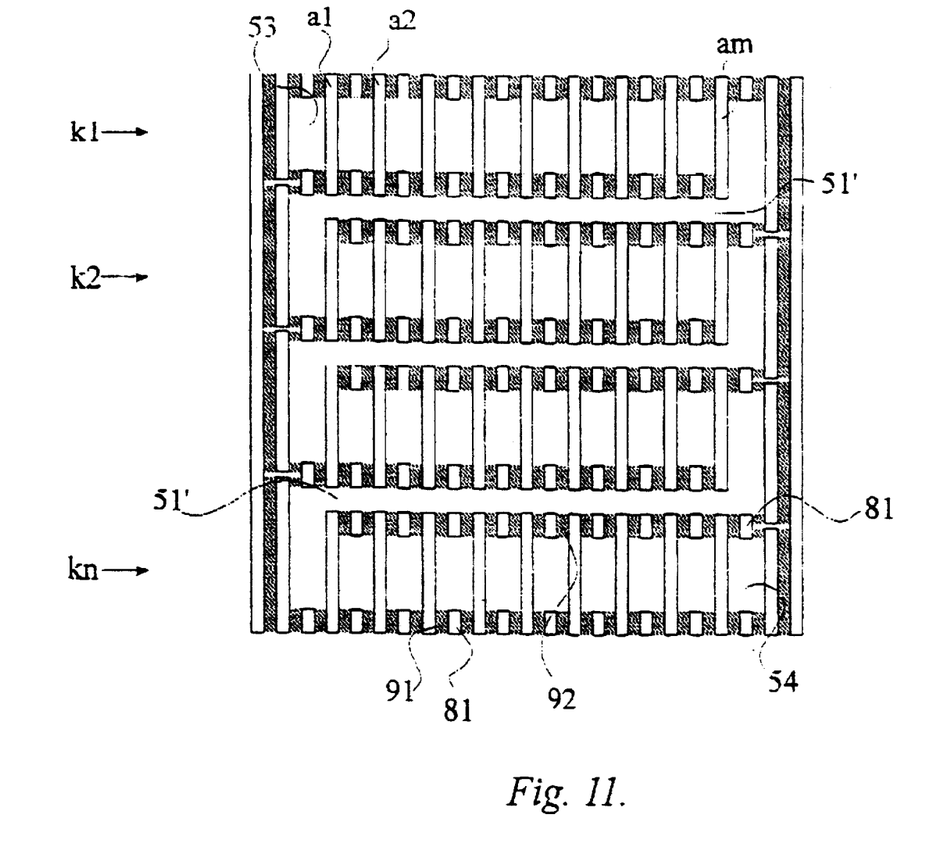
FIG. 11 illustrates schematically and from above the manner in which electrically conductive and electrically insulating ridges co-act to form a detector that may include a plurality of columns of conductive ridges.

FIG. 10 shows an embodiment where the electrical interconnection 51 between two ridges in two mutually adjacent columns K1, K2 can be achieved by means of an electrically conductive surface section 51 that has been prepared to make this interconnection FIG. 11 illustrates a method of fabricating a generally square thermocouple, by combining conductive ridges a1, a2 with insulating ridges 81.

According to the present invention, the series of conductive ridges form the series-connected thermocouples where the metal layer on a first or a second side surface of a first conductive ridge K1, a1, or on a conductive surface adjacent said first conductive ridge, in said series of conductive ridges forms a first connecting electrode 53 on the series connected thermocouple, and a first or a second surface belonging to a last conductive ridge Kn, am, or a conductive surface on a ridge adjacent said last conductive ridge, in said series of conductive ridges forms a second connecting electrode 54 on the series-connected thermocouple.

Figure 12:
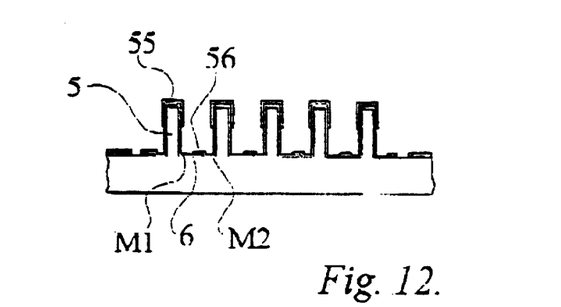
FIG. 12 illustrates schematically and in side view the manner in which conductive ridges can be adapted to absorb incident light rays.

As illustrated in FIG. 12, when the detector 3 is intended to detect light rays within the infrared wavelength range, the three-dimensional structure can be further worked by covering the upper surface 5c of a respective conductive ridge with a heat-absorbent layer 55, and by covering the respective intermediate conductive surfaces 6 with a heat reflecting layer 56.

This is done so that the hot solder points which form measuring points in the thermocouple and which are exposed to the incident light rays will absorb the greatest possible amount of the thermal energy contained in the incident light rays. The cold solder points, i.e. the conductive surfaces between the conductive ridges, shall not be subjected to the effect of incident light rays and are therefore shadowed by the conductive ridges, as before described. However, it is possible that stray light may occur in the surroundings of the detector, and consequently it is desirable to cover the cold solder points with a heat-reflecting layer.

According to one preferred embodiment of the invention, the heat-absorbent coating 55 is comprised of a layer of carbon, and the heat-reflecting layer 56 is comprised of the reflective metal layers M1, M2.

The tow metals M1, M2 used shall be appropriate both with respect to optical properties, reflection of utilised light rays, and also with respect to their thermoelectric properties. Thus, the first metal M1 shall differ from the second metal M2 and the metals shall provide a thermoelectrical effect in co-operation with each other.

According to one embodiment, the two metals are gold and chromium respectively, where chromium is the first, innermost metal M1 and gold is the second metal M2.

In the case of the illustrated embodiment, in which the component is a thermocouple, it is shown by way of example that in some respects a polymeric material has more appropriate properties than silicon for instance, which does not possess the desired thermally insulating properties.

Described below are two further components that can be constructed by means of an inventive method, with the intention of further facilitating and understanding of the present invention.

Figure 13:
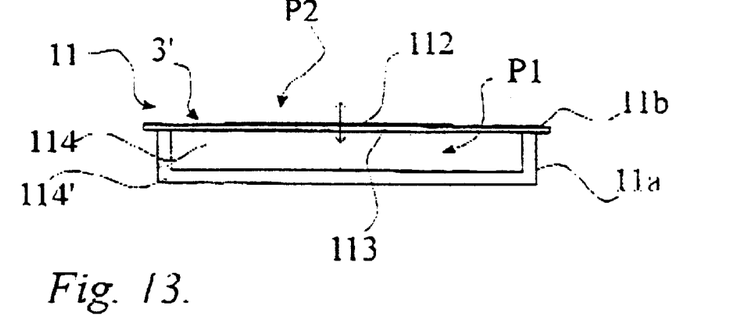
FIG. 13 is a schematic, simplified illustration of a component in the form of a pressure sensor that includes a cavity and a strain gauge.

The component illustrated in FIG. 13 is a pressure sensor 11 which includes a strain gauge 112 and which is mounted on the outer surface of a wall 113 belonging to a closed cavity 114. The wall 113 is sufficiently thin for its projection from the cavity to change in response to the pressure difference between a gas pressure P1 enclosed within the cavity and a fluctuating gas pressure P2 outside said cavity.

In the case of this embodiment, the substrate and its three-dimensional structure 3' includes the body 114' that defines the cavity 114, and further treatment or processing of the substrate comprises covering the thin wall 113 with a metal strip that forms the strain gauge 112.

For manufacturing reasons, the cavity in the pressure sensor 11 will often comprise two parts 11a, 11b, where one part 11a has a box-like shape and the other part 11b has the form of a box lid. The thin wall 113 will often be formed by a membrane applied to the lid 11b or to the bottom of the box 11a.

There is nothing to prevent a component produced in accordance with the present invention from consisting of several parts, for instance box and lid, of which one or more are manufactured in accordance with the present invention. Further working of the substrate will then comprise joining the component parts together. This can be achieved, for instance by curing, hardening, glue in UV light, by ultra-sound welding, or by chemically or physically working the surfaces so as to enable said surfaces to be joined together more readily, said three-dimensional structure having been adapted to enable said parts to be joined together by the method used.

An alternative, particularly advantageous method of joining the component parts together in accordance with the invention is to create surfaces that are so smooth that when coated with a metal, such as gold, they will wring together without requiring further processing. A wringing joint is achieved when bringing together two surfaces that are so smooth as to obtain a direct atomic bond between said surfaces. The flexibility possessed by a polymeric material means that any irregularities or even contaminants can be taken-up by the flexibility of the plastic, which is not possible when using a silicon or quartz substrate, for instance.

Figure 14:
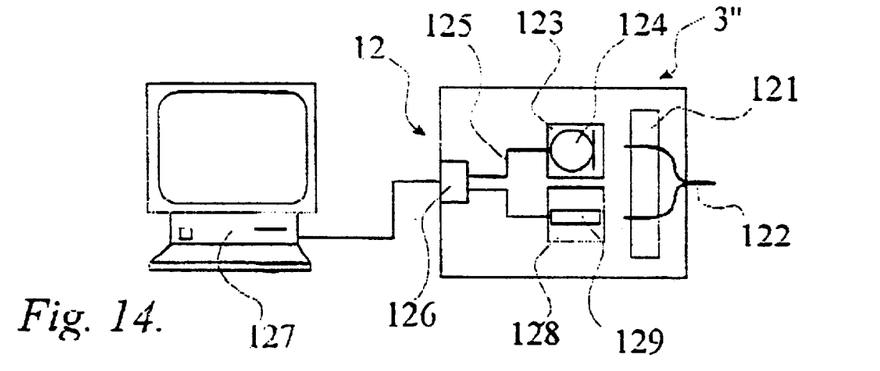
FIG. 14 is a schematic, highly simplified illustration of a component in the form of an electro-optic switching unit and associated parts.

FIG. 14 is a highly simplified and schematic illustration of a component in the form of an electro-optical coupling unit 12, which may, for instance, be adapted for broadband information transmission. With such a coupling unit, it is desirable to be able to manufacture low-cost components for managing, e.g., optically carried information to the home.

The three-dimensional structure 3" of the substrate for such a component 12 shall include mechanical alignment 121 of an optical fibre 122, and a first holder 123 for a photodiode 124 which is adapted to convert information in the optical domain to an electric signal.

The three-dimensional structure 3" enables electrical conductor paths 125 and a connection terminal 126 to be formed, thereby enabling the electrical signals to be switched to an external unit 127, such as a computer.

Reverse signal order will, of course, also be required when electrically carried information shall generate light pulses from a light source and the light coupled to the optical fibre.

The three-dimensional structure 3" shall therefore also include a second holder 128 for a light source 129, said holder being adapted to align the light source 129 with the optical fibre 122, or the optical fibre mechanical alignment means 121.

The illustrated component 12 may be produced in accordance with the present invention, by initially giving the substrate a three-dimensional structure 3" that fulfills all geometrical requirements with respect to the mechanical alignment 121 of the optical fibre 122, the first holder 123 for the photodiode 124, and the second holder 128 for the light source 129.

Requisite electrical conductor paths 125 and the application of the optical fibre 122, the photodiode 124, the light source 129 and the connection terminal 126 are implemented by said further working operations with the aid of processes earlier described, with further working being made possible by virtue of appropriate dimensioning of the three-dimensional structure 3".

According to one embodiment of the invention, the optical fibre 122 may be formed as an optical waveguide in the substrate by direct connection with the photodiode 124 and the light source 129. However, a connection between the externally arriving optical fibre and the thus formed optical waveguide is still preferred.

Figure 15:
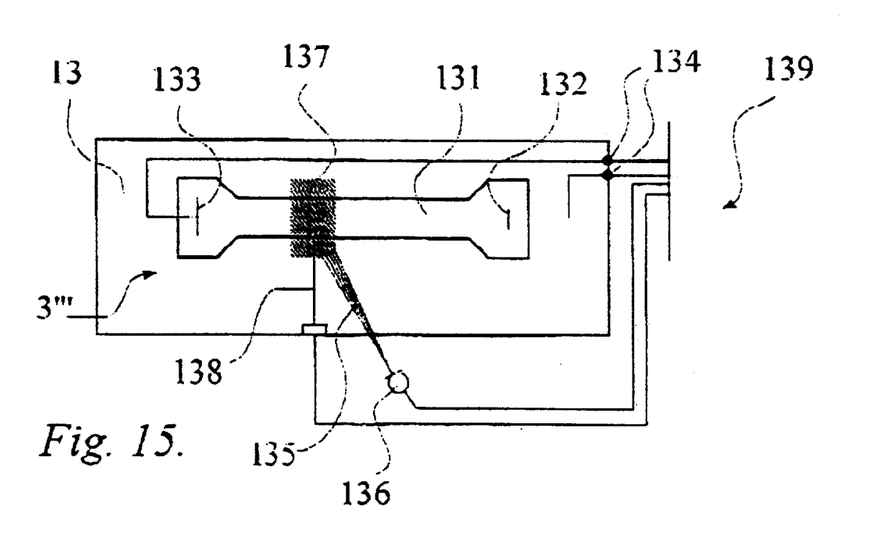
FIG. 15 is a schematic, highly simplified illustration of a component in the form of a test channel adapted for use with a biochemical analyser based on electrophoretic separation.

FIG. 15 illustrates an example of a biochemical analyser based on electrophoretic separation. In its simplest form, the analyser requires a component 13 that includes a channel structure in which a separating hydrogel is placed by filling the channel with the gel in a monomer form and then polymerising appropriate regions of the gel with the aid of UV light.

Separation is effected by applying an electric field and therewith causing the molecules to migrate along the channel and sieving said molecules in said gel. Different molecules will migrate at different speeds, in relation to their size and charge. In general, larger molecules will migrate more slowly than smaller molecules, while molecules having a high electrical charge will migrate more quickly.

The relevant three-dimensional structure 3''' for this application is comprised of a mechanical channel structure 131 that has been produced by the aforedescribed replication technique. An anode 132 and a cathode 133 can be connected electrically at respective ends of the channel 131 by an electrode pattern that has been produced by shadow masking or lithographic technique, as described earlier with reference to other embodiments. The three-dimensional structure for this component will therefore include the channel 131 and enable an anode 132 and a cathode 133 with associated electric connections 134 to be formed.

Subsequent to separation, the molecules are preferably detected by optical methods, for instance by absorbence or fluorescence. In this latter case, large gains can be made if the fluorescent light 135 can be collected effectively by the intended detector 136.

This can be achieved, for instance, by placing a collecting lens in the three-dimensional structure 3''', with the aid of a diffractive optical element 137 having appropriate properties. Alternatively, the three-dimensional structure 3''' may provide possibilities of forming optical waveguides 138, so as to enable the light required for the fluroescence to be conducted to the channel 131 from an external source, for instance.

The component 13 may also be adapted for co-action with a lid or cover that closes the channel.

There is obtained in this way an electrophoretic separation component that includes sample channels 131, electrodes 132, 133 having connections 134, optical waveguides 135 for conducting light to the channel 131 from an external light source, and a diffractive optical element 137 for focusing the spread fluorescent light 135 onto an external detector 136. The expensive components, such as light source, normally a laser, and detector 136, with associated electronics thus belong to an instrument 139 which is adapted to co-act with the cheaper components produced in accordance with the invention.

Working of that part of the die or the model to be used in manufacturing that part of the three-dimensional structure 3''' which corresponds to the diffractive optical element 137 may, e.g. be achieved by electron beam lithography.

It will be understood that further working or further processing of all described embodiments may also include mounting of different integrated circuits, such as logic circuits, Asics, amplifiers and the like, where said three-dimensional structure is adapted to allow the fitting of such components.

It will therefore be understood that the invention is not restricted to the aforedescribed and illustrated embodiments thereof and that modifications can be made within the scope of the inventive concept as defined in the following Claims.

What is claimed is:

1. A method of producing an electric, electronic, optical and/or mechanical component where a die or mould is used, where the substrate for said component is given a three-dimensional structure or shape, and where the substrate is adapted for further treatment or processing to build said component, characterised in that said substrate is formed by shaping said substrate against said die or mould, such as by moulding, pressing, extruding or embossing said substrate;

that at least a part of said die or mould that corresponds to said component is produced by shaping against a model of said structure, e.g. by moulding or electroplating; that said model is produced by micromechanically working a material that has been suitably prepared to this end; and in that the three-dimensional structure or configuration of said model is chosen so as to correspond to desired component-associated surface parts, electric conductor paths, and/or further electric and/or electronic circuits;

or that at least a part of said die or mould that corresponds to said component is produced by micromechanically working a material that is suitable for such working;

and in that the three-dimensional structure or configuration of said die or mould is complementary in relation to desired component-associated surface parts, electric conductor paths and/or further electric and/or electronic circuits.

2. A method according to claim 1, characterised by producing said component on a delimited surface region; and by producing electrical conductor paths and/or further electrical and/or electronic components on said delimited surface region in mutually the same manner.

3. A method according to claim 2, characterised by providing said component with mechanical parts, such as snap-fastener means, and projections and recesses intended for fitting said component to a base structure.

4. A method according to claim 1, characterised in that the substrate is comprised of a polymeric material.

5. A method according to claim 1, characterised in that the micromechanically workable material is silicon.

6. A method according to claim 1, characterised in that the micromechanically workable material is quartz.

7. A method according to claim 1, characterised in that said further treatment or processing includes the use of a lithographic process.

8. A method according to claim 1, characterised in that said further treatment or processing includes the use of a PVD process.

9. A method according to claim 1, characterised in that said further treatment or processing includes the use of a CVD process.

10. A method according to claim 1, characterized in that said further treatment or processing includes the use of a doping process, such as ion-implantation.

11. A method according to claim 1, characterised in that said further treatment or processing includes the use of an etching process, such as an ion-etching, chemical-etching or plasma-etching process.

12. A method according to claim 9, characterised in that said process is applied at a specific application angle in relation to said three-dimensional structure, such as to form processed and/or non-processed surface regions by virtue of the shading effects thus obtained.

13. A method according to claim 12, characterised by using two or more application angles, such as to form a pattern of different processed regions.

14. A method according to claim 1, characterised in that said further treatment or processing includes the use of a mechanical working process.

15. A method according to claim 6, characterised in that said further treatment or processing includes the use of a combination of one or more treatments or processes according to any one of claims 6 to 14.

16. A method according to claim 1, where a produced component is a thermocouple, characterised by coating at least said three-dimensional structure that presents a surface region or surface regions with a first and a second electrically conductive metal; applying said first metal coating to said three-dimensional structure at a first application angle other then 90°; applying said second metal layer to said three-dimensional structure at a second application angle other than 90° and different to said first application angle, said first and said second metal layers being caused to overlap each other within discrete detector-associated surface parts; and giving the three-dimensional structure and/or configuration having a such applied electrically conductive layer the function of one or more thermocouples.

17. A method according to claim 16, characterised by providing the three-dimensional structure with a plurality of so-called conductive ridges that include a first side surface, a second side surface and an upper side surface, and an intermediate so-called conductive surface between respective adjacent conductive ridges; adapting said first angle so that said first side surface and at least a part of said upper surface of respective conductive ridges and at least a part of said respective intermediate conductive surfaces are coated with said first metal layer; adapting said second angle so that said second side surface and at least a part of said upper surface of respective conductive ridges and at least a part of respective intermediate conductive surfaces are coated with said second metal layer; adapting said first and said second angles so that said second metal layer overlaps, and establishes an electric contact with, said first metal layer on said upper surface of respective conductive ridges and on respective intermediate conductive surfaces, such that said metal layers will form a series of electrically interconnected junctions between said first and said second metal layers.

18. A method according to claim 17, characterised by positioning said three-dimensional structure relative to incident light rays, or electromagnetic waves, to be detected, such that said incident light rays will irradiate said upper surface of respective conductive ridges and so that said intermediate conductive surfaces will be located in the shadow of said conductive ridges with respect to said incident light rays.

19. A method according to claim 17, characterised by forming electrically insulating surface sections between said conductive ridges with said intermediate conductive surfaces and surrounding surface sections belonging to said base structure.

20. A method according to claim 19, characterised by positioning so-called insulating ridges having mutually adjacent so-called insulating surfaces relative to one another and relative to said conductive ridges and relative to said first and said second angles in a manner such that a coating of both said first and said second metals will be excluded on said insulating surfaces and therewith achieve said electrical insulation.

21. A method according to claim 17, characterised by giving the conductive ridges a configuration that forms n-number of columns of conductive ridges, said columns being designated column 1, column 2, etc., up to column "n", wherein respective columns include m-number of conductive ridges designated ridge 1, ridge 2, etc., up to ridge "m", where "m" may be different for respective columns; in that the first ridge in each column, with the exception of the "n"th column, and that the "m"th ridge in each column, with the exception of the last column, form interconnected ridges, where the "m"th ridge in each column, with the exception of the last column, is connected electrically with the first ridge of the next-following column, and in that the junctions between said first and said second metal layers belonging to all conductive ridges within all columns form said series of electrically interconnected junctions.

22. A method according to claim 21, characterised in that said electrical connection between an "m"th ridge in a column and a ridge in an adjacent column is effected by forming an electrically conductive surface section between said adjacent columns; and in that said conductive surface section is electrically connected with interconnected ridges of adjacent columns but is electrically insulated from said adjacent columns in other respects.

23. A method according to claim 17, characterised in that said series of conductive ridges forms a series-connected thermocouple; in that the metal layer on a first or a second side surface of a first conductive ridge or a conductive surface adjacent said first conductive ridge in said series of conductive ridges forms a first connecting electrode for said thermocouple; and in that a first or a second side surface of a last conductive ridge for a conductive surface adjacent said last conductive ridge in said series of conductive ridges forms a second thermocouple connecting electrode.

24. A method according to claim 17, characterised in that the upper surface of respective conductive ridges is coated with a heat-absorbent layer; and in that said intermediate conductive surface is coated with a heat-reflecting layer.

25. A method according to claim 24, characterised in that said heat-absorbent layer is comprised of carbon; and in that said heat-reflecting layer is comprised of said metal layers.

26. A method according to claim 17, characterised in that the metal in said first layer differs from the metal in said second layer; and in that a thermoelectric effect is obtained between said first and said second metal layers.

27. A method according to claim 26, characterised in that the two metal layers are comprised of gold covering chromium.

28. A method according to claim 1, where a produced component is a pressure sensor that includes a strain gauge mounted on the outside of a wall belonging to a closed cavity and which is of such thinness as to change its projection from said cavity in response to the difference in pressure between a gas pressure prevailing in said cavity and a gas pressure prevailing outside said cavity, characterised in that said three-dimensional structure forms said cavity; and in that said further treatment or processing of said substrate involves applying to said thin wall a metal strip that forms said strain gauge.

29. A method according to claim 1, where a produced component is an electro-optical coupling unit adapted for mechanically aligning an optical fibre, a photodiode and a light source in relation to one another, characterised in that the three-dimensional structure is constructed to satisfy the geometric requirements for holding said optic fibre, photodiode and light source in mutually aligned relationship; and in that said three-dimensional structure is adapted for implementing requisite electric conductor paths and for application of the optic fibre, photodiode and light source by said further treatment or processing.

30. A method according to claim 1, where a produced component is intended for a biochemical analyser based on electrophoretic separation and includes a channel structure in which a separating hydrogel is placed, and where molecules intended for analysis are sieved in said gel by causing said molecules to migrate along the channel between an electric field applied between two electrodes, characterised in that said three-dimensional structure includes said channel; and in that said three-dimensional structure is adapted for implementation of said electrodes and associated connection conductors by said further treatment or processing.

31. A method according to claim 30, characterised in that said three-dimensional structure is adapted for implementation of waveguides intended to conduct necessary light to said channel from an external light source, and for implementation of a diffractive optical element intended for focusing fluorescent, spread light onto an external detector, by said further treatment or processing.

\* \* \* \* \*